(12) United States Patent
Kahn et al.

(10) Patent No.: US 8,604,018 B2
(45) Date of Patent: *Dec. 10, 2013

(54) ALPHA-HELIX MIMETICS AND METHODS RELATING TO THE TREATMENT OF FIBROSIS

(75) Inventors: Michael Kahn, Altadena, CA (US); Masakatsu Eguchi, Bellevue, WA (US)

(73) Assignee: Institute for Chemical Genomics, Altadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/073,176

(22) Filed: Mar. 28, 2011

(65) Prior Publication Data

US 2012/0059010 A1    Mar. 8, 2012

Related U.S. Application Data

(63) Continuation of application No. 11/908,961, filed as application No. PCT/US2006/009191 on Mar. 15, 2006, now Pat. No. 7,915,251.

(60) Provisional application No. 60/663,499, filed on Mar. 18, 2005.

(51) Int. Cl.
    *A61K 31/553*      (2006.01)
    *A61K 31/554*      (2006.01)
    *A61K 31/519*      (2006.01)

(52) U.S. Cl.
    USPC .................................. 514/211.09; 514/262.1

(58) Field of Classification Search
    USPC ........... 514/511.09, 262.1; 540/524; 544/256, 544/282

See application file for complete search history.

(56) References Cited

U.S. PATENT DOCUMENTS 7,915,251 B2 *   3/2011   Kahn et al. ............... 514/211.09
2008/0009500 A1    1/2008   Kahn

FOREIGN PATENT DOCUMENTS

| WO | WO 97/15577 | 5/1997 |
| WO | WO 01/00210 | 1/2001 |
| WO | WO 01/16135 | 3/2001 |

OTHER PUBLICATIONS

Dörwald, Florencio Zaragoza, "Side Reactions in Organic Synthesis: A Guide to Successful Synthesis Design," WILEY-VCH Verlag GmbH & Co. KGaA, 2005, Preface.

* cited by examiner

*Primary Examiner* — Paul Zarek
(74) *Attorney, Agent, or Firm* — Barry L. Davison; Davis Wright Tremaine LLP

(57) ABSTRACT

The invention provides α-helix mimetic structures and a chemical library relating thereto. The compounds, pharmaceutical compositions comprising the compounds, and methods of the invention using the compounds, relate to the treatment of diseases including fibrosis, such as pulmonary fibrosis.

9 Claims, 4 Drawing Sheets

ALPHA-HELIX MIMETICS AND METHODS RELATING TO THE TREATMENT OF FIBROSIS

CROSS REFERENCE TO RELATED APPLICATION(S)

This application is a continuation of U.S. patent application Ser. No. 11/908,961 filed 20 Jun. 2008 (issued as U.S. Pat. No. 7,915,251), which is the United States nationalization, under 35 U.S.C. §371, of International Application No. PCT/US2006/009191, filed 15 Mar. 2006, which claims the benefit of priority to U.S. Provisional Patent Application Ser. Nos. 60/663,499 filed 18 Mar. 2005, all of which are incorporated by reference herein in their entirety.

STATEMENT REGARDING FEDERALLY SPONSORED RESEARCH OR DEVELOPMENT

This invention was made with government support under grant R01 HL073722 awarded by the National Institutes of Health. The government has certain rights in the invention.

TECHNICAL FIELD

The present invention relates generally to α-helix mimetic structures and to a chemical library relating thereto. The invention also relates to applications in the treatment of diseases and pharmaceutical compositions comprising them.

BACKGROUND OF THE INVENTION

Fibrosis can occur in the lung, liver, kidney, eye, heart, and other major organs of the body. Fibrosis can be due to toxic or infectious injury, such as cigarette smoke to the lungs or viral hepatitis infection of the liver. The cause of some fibrotic diseases is unknown, which is the case with idiopathic pulmonary fibrosis.

Idiopathic pulmonary fibrosis (IPF) is a chronic and insidious inflammatory disease of the lung that kills most of its victims within five years after diagnosis. IPF afflicts 83,000 Americans and more than 31,000 new cases develop each year. It is believed that death due to IPF is greatly underreported and the considerable morbidity of IPF is not recognized. IPF represents just one of the many fibrotic diseases that occurs as a result of chronic inflammation. It is estimated by the United States government that 45% of all deaths in the U.S. can be attributed to fibrotic disorders, and therapeutic agents are needed for treating this condition, especially fibrotic disease of the lungs.

Pulmonary fibrosis leads to progressive scarring and lung destruction. Currently, there are five million people worldwide that are affected by pulmonary fibrosis with 50% mortality at 5 years after diagnosis (Katzenstein A and Meyers Am. J. Respir. Crit. Care Med. 1998, 157, 130-1-15 and American Thoracic Society, Am. J, Respir. Care Med. 2000, 161, 646, 664.). Pulmonary fibrosis is believed to be initiated by insult to the lung parenchyma (either acute or chronic) and develop in patients unable to effectively heal the damage (Gross T. J. N. Eng. J Med 345, 517, 2001). The fibrosis is refractory to corticosteroids and no effective therapy currently exists.

Random screening of molecules for possible activity as therapeutic agents has occurred for many years and resulted in a number of important drug discoveries. While advances in molecular biology and computational chemistry have led to increased interest in what has been termed "rational drug design", such techniques have not proven as fast or reliable as initially predicted. Thus, in recent years there has been a renewed interest and return to random drug screening. To this end, particular strides having been made in new technologies based on the development of combinatorial chemistry libraries, and the screening of such libraries in search for biologically active members.

In general, combinatorial chemistry libraries are simply a collection of molecules. Such libraries vary by the chemical species within the library, as well as the methods employed to both generate the library members and identify which members interact with biological targets of interest. While this field is still young, methods for generating and screening libraries have already become quite diverse and sophisticated. For example, a recent review of various combinatorial chemical libraries has identified a number of such techniques (Dolle, J. Com. Chem., 2(3): 383-433, 2000), including the use of both tagged and untagged library members (Janda, Proc. Natl. Acad. Sci. USA 91:10779-10785, 1994).

Initially, combinatorial chemistry libraries were generally limited to members of peptide or nucleotide origin. To this end, the techniques of Houghten et al. illustrate an example of what is termed a "dual-defined iterative" method to assemble soluble combinatorial peptide libraries via split synthesis techniques (Nature (London) 354:84-86, 1991; Biotechniques 13:412-421, 1992; Bioorg. Med. Chem. Lett. 3:405-412, 1993). By this technique, soluble peptide libraries containing tens of millions of members have been obtained. Such libraries have been shown to be effective in the identification of opioid peptides, such as methionine- and leucine-enkephalin (Dolley and Houghten, Life Sci. 52, 1509-1517, 1993), and N-acylated peptide library has been used to identify acetalins, which are potent opioid antagonists (Dooley et al., Proc. Natl. Acad. Sci. USA 90:10811-10815, 1993). More recently, an all D-amino acid opioid peptide library has been constructed and screened for analgesic activity against the mu ("μ") opioid receptor (Dooley et al., Science 266:2019-2022, 1994).

While combinatorial libraries containing members of peptide and nucleotide origin are of significant value, there is still a need in the art for libraries containing members of different origin. For example, traditional peptide libraries to a large extent merely vary the amino acid sequence to generate library members. While it is well recognized that the secondary structures of peptides are important to biological activity, such peptide libraries do not impart a constrained secondary structure to its library members.

To this end, some researchers have cyclized peptides with disulfide bridges in an attempt to provide a more constrained secondary structure (Tumelty et al., J. Chem. Soc. 1067-68, 1994; Eichler et al., Peptide Res. 7:300-306, 1994). However, such cyclized peptides are generally still quite flexible and are poorly bioavailable, and thus have met with only limited success.

More recently, non-peptide compounds have been developed which more closely mimic the secondary structure of reverse-turns found in biologically active proteins or peptides. For example, U.S. Pat. No. 5,440,013 to Kahn and published PCT WO94/03494, PCT WO01/00210A1, and PCT WO01/16135A2 to Kahn disclose conformationally constrained, non-peptidic compounds, which mimic the three-dimensional structure of reverse-turns.

While significant advances have been made in the synthesis and identification of conformationally constrained, reverse-turn mimetics, there remains a need in the art for small molecules, which mimic the secondary structure of peptides. There has been also a need in the art for libraries containing such members, as well as techniques for synthesizing and screening the library members against targets of interest, particularly biological targets, to identify bioactive library members. For example, U.S. Pat. No. 5,929,237 and its continuation-in-part U.S. Pat. No. 6,013,458 to Kahn also discloses conformationally constrained compounds which mimic the secondary structure of reverse-turn regions of biologically active peptides and proteins. The synthesis and identification of conformationally constrained α-helix mimetics and their application to diseases are discussed in Walensky, L. D. et al *Science* 305, 1466, 2004; Klein, C. *Br. J. Cancer.* 91:1415, 2004.

Many models of pulmonary fibrosis have been developed, however regardless of the nature of the initial insult the stages of progression appear to be quite similar. A generally accepted model involves damage to the endothelial and type I alveolar epithelial cells followed by interstitial edema, deposition of fibrous materials in the alveolus in areas of loss of type I epithelial cells. It is believed that limited proliferation of the type II cells and subsequent differentiation into type I and Clara cells is critical to reestablishment of normal gas exchange.

Anti-inflammatory therapies (e.g. corticosteroids, interferon-γ) to treat pulmonary fibrosis have been disappointing to date due to limited efficacy and severe adverse side effects. An important unmet need exists to identify the key molecular pathways involved in the development and progression of pulmonary fibrotic diseases and to develop new therapeutic agents to prevent the progression and reverse the disease process. No drugs have been approved for the treatment of any fibrotic disease in the United States. Research and development is desperately needed to provide treatments to those afflicted with fibroproliferative diseases. The present invention fulfills these needs, and provides further related advantages by providing conformationally constrained compounds which mimic the secondary structure of α-helix regions of biologically active peptides and proteins.

SUMMARY OF THE INVENTION

In brief, the present invention is directed to conformationally constrained compounds, which mimic the secondary structure of α-helix regions of biologically active peptides and proteins and their use for treating fibrosis, such as pulmonary fibrosis. This invention also discloses libraries containing such compounds, as well as the synthesis and screening thereof.

The compounds of the present invention have the following general formula (I):

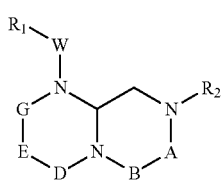

Wherein A is —(C=O)—CHR$^3$—, B is N—R$_4$—, D is —(C=O)—(CHR$_5$)— or —(C=O)—, E is —(ZR$_6$)— or (C=O), G is —(XR$_7$)$_n$—, —(CHR$_7$)—(NR$_8$)—, —(C=O)—(XR$_9$)—, or —(C=O)—, W is —Y(C=O)—, —(C=O)NH—, —(SO$_2$)— or nothing, Y is oxygen or sulfur, X and Z is independently nitrogen or CH, n=0 or 1; and R$_1$, R$_2$, R$_3$, R$_4$, R$_5$, R$_6$, R$_7$, R$_8$, and R$_9$ are the same or different and independently selected from an amino acid side chain moiety or derivative thereof, the remainder of the molecule, a linker and a solid support, and stereoisomers thereof.

In the embodiment wherein A is —(C=O)—CHR$^3$—, B is —(NR$_4$)—, D is —(C=O)—, E is —(ZR$_6$)—, and G is —(C=O)—(XR$_9$)—, the compounds of this invention have the following formula (III):

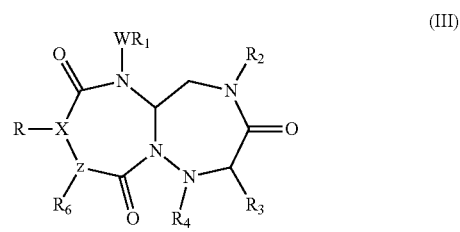

Wherein W, Y and n are as defined above, Z is nitrogen or CH (when Z is CH, then X is nitrogen), and R$_1$, R$_2$, R$_3$, R$_4$, R$_6$, and R$_9$ are as defined in the following detailed description.

In the embodiment wherein A is —(C=O)—(CHR$_3$), B is —(CHR$_4$)—, D is —(C=O)—, E is —(ZR$_6$)—, and G is (XR$_7$)$_n$—, the compounds of this invention have the following general formula (IV):

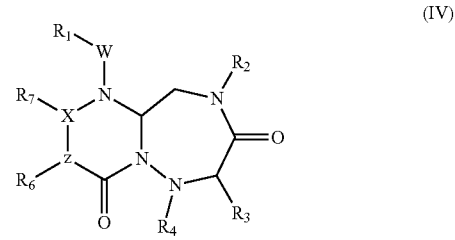

Wherein W, Y and n are as defined above, Z is nitrogen or CH (when Z is nitrogen, then n is zero, and when Z is CH, then X is nitrogen and n is not zero), and R$_1$, R$_2$, R$_4$, R$_6$, and R$_7$, are as defined in the following detailed description.

The present invention is also directed to libraries containing compounds of formula (I) above, as well as methods for synthesizing such libraries and methods for screening the same to identify biologically active compounds. Compositions containing a compound of this invention in combination with a pharmaceutically acceptable carrier or diluent are also disclosed.

Especially, the present invention relates pharmaceutical compositions containing compounds of formula (I) for treating disorders including fibrosis of the lung. It further relates to methods for treating disorders including fibrosis of the lung which are associated with TGF-β signaling pathway.

The compound V (ICG-001) is useful for treating fibrosis as described in Example 1.

These and other aspects of this invention will be apparent upon reference to the attached figures and following detailed description. To this end, various references are set forth herein, which describe in more detail certain procedures, compounds and/or compositions, and are incorporated by reference in their entirety.

BRIEF DESCRIPTION OF THE FIGURES

FIG. 1B) intracheal bleo+ICG-001; FIG. 1 C) saline+saline.

DETAILED DESCRIPTION OF THE INVENTION

Figure 1:
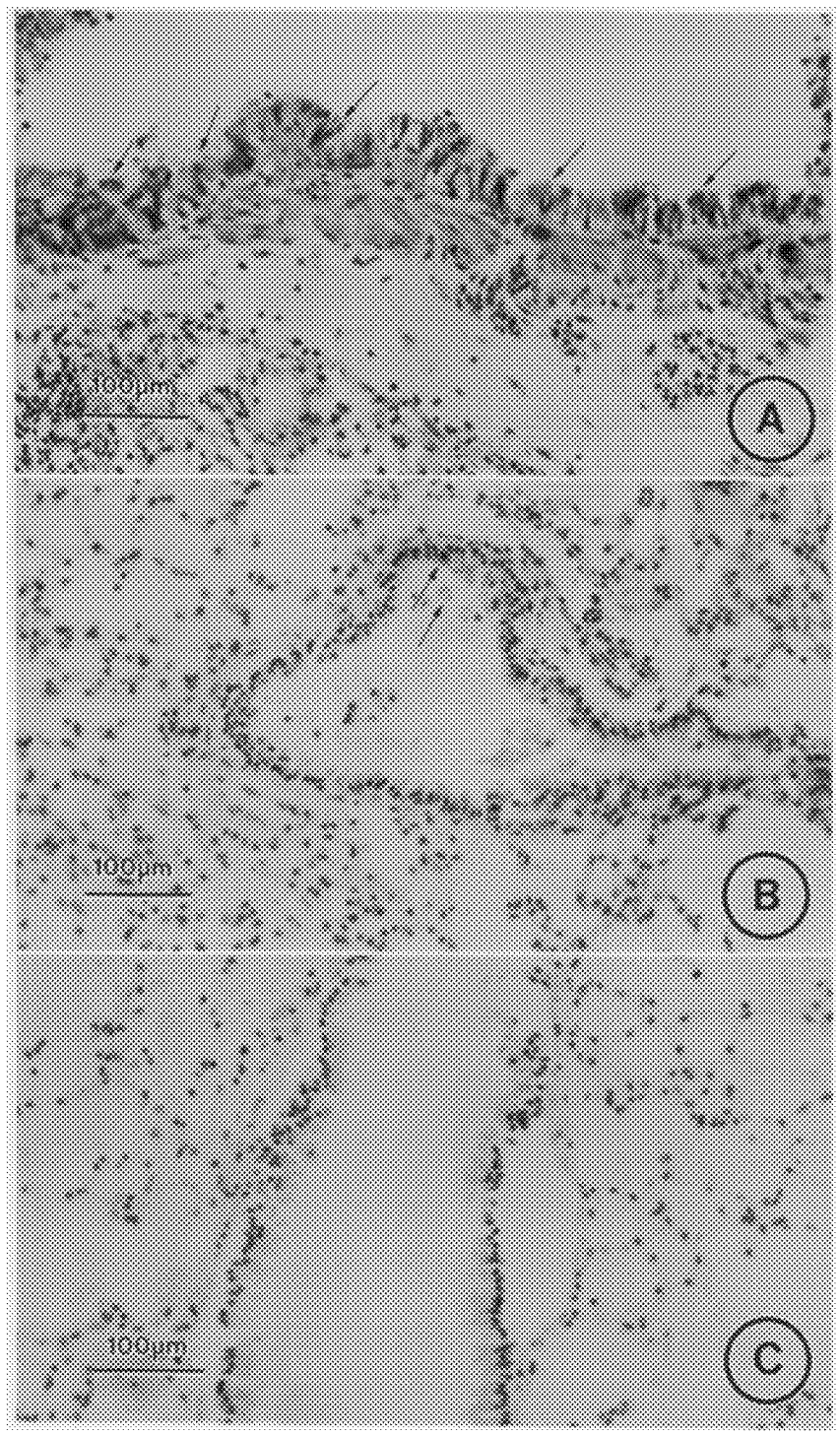
FIG. 1 depicts lung sections taken from Bat-Gal transgenic mice given intratracheal saline or bleomycin and either treated with ICG-001 (5 mgs/Kg/day subcutaneously) or saline as vehicle control. The lungs were sectioned and stained with X-Gal (blue color.) FIG. 1A) intratracheal bleo+saline.

Transforming growth factor β (TGFβ), a key mediator in the development of fibrosis, is important in cell proliferation and differentiation, apoptosis, and deposition of extracellular matrix (ECM). TGFβ signaling activates both the Smad and AP-1 transcription pathways. TGFβ in the airways of patients with pulmonary fibrosis (PF) may function initially as a "healing molecule" involved in the diminution of initial airway inflammation and in tissue repair. However, with continued inflammatory response such as may occur in PF, the balance may be shifted, to excessive ECM deposition and development of airway fibrosis.

Fibroproliferative diseases are generally caused by the activation of resident stellate cells which are found in most organs. This activation of stellate cells leads to their conversion to myofibroblasts which display characteristics of muscle and non-muscle cells. Activated stellate cells initiate inflammatory signals, principally mediated through TGF-β. Inflammatory cytokines and mediators in addition to TGF-β, lead to proliferation of myofibroblasts. Stellate-derived myofibroblasts proliferate and replace healthy, functional organ cells with extra-cellular matrix that exhibit muscle and connective tissue traits. Ultimately, organ failure results when the nonfunctional fibrotic honeycomb matrix replaces a critical number of healthy cells.

The initial cause of fibrosis is believed to be the result of injury or insult to organ tissues. This cellular injury to organ tissues can often be traced to toxic or infectious agents. Pulmonary fibrosis, or interstitial lung disease, is often the result of smoking, chronic asthma, chronic obstructive pulmonary disease (COPD) or pneumonia.

Pulmonary fibrosis destroys the lung's ability to transport oxygen and other gases into or out of the blood. This disease modifies the delicate and elastic tissues of the lung, changing these tissues into thicker, stiff fibrous tissue. This change or replacement of the original tissue is similar to the permanent scarring that can occur to other damaged tissues. Scarring of the lung reduces the lung's ability to allow gases to pass into or out of the blood (i.e. oxygen, carbon dioxide). Gradually, the air sacs of the lungs become replaced by fibrotic tissue. When the scar forms, the tissue becomes thicker causing an irreversible loss of the tissue's ability to transfer oxygen into the bloodstream. Symptoms include shortness of breath, particularly with exertion; chronic dry, hacking cough; fatigue and weakness; discomfort in the chest; loss of appetite; and rapid weight loss.

Several causes of pulmonary fibrosis are known and they include occupational and environmental exposures. Many jobs, particularly those that involve mining or that expose workers to asbestos or metal dusts, can cause pulmonary fibrosis. Workers doing these kinds of jobs may inhale small particles (like silica dusts or asbestos fibers) that can damage the lungs, especially the small airways and air sacs, and cause the scarring associated with fibrosis. Agricultural workers also can be affected. Some organic substances, such as moldy hay, cause an allergic reaction in the lung. This reaction is called Farmer's Lung and can cause pulmonary fibrosis. Other fumes found on farms are directly toxic to the lungs.

Another cause is Sarcoidosis, a disease characterized by the formation of granulomas (areas of inflammatory cells), which can attack any area of the body but most frequently affects the lungs. Certain medicines may have the undesirable side effect of causing pulmonary fibrosis, as can radiation, such as treatment for breast cancer. Connective tissue or collagen diseases such as rheumatoid arthritis and systemic sclerosis are also associated with pulmonary fibrosis. Although genetic and familial factors may be involved, this cause is not as common as the other causes discussed above. In Chronic Obstructive Pulmonary Disease (COPD), connective tissue proliferation and fibrosis can characterize severe COPD. COPD can develop as a result of smoking or chronic asthma.

When all known causes of interstitial lung disease have been ruled out, the condition is called "idiopathic" (of unknown origin) pulmonary fibrosis (IPF). Over 83,000 Americans are living with IPF, and more than 31,000 new cases develop each year. This debilitating condition involves scarring of the lungs. The lungs' air sacs develop scar, or fibrotic tissue, which gradually interferes with the body's ability to transfer the oxygen into the bloodstream, preventing vital organs and tissue from obtaining enough oxygen to function normally.

There are several theories as to what may cause IPF, including viral illness and allergic or environmental exposure (including tobacco smoke). These theories are still being researched. Bacteria and other microorganisms are not thought to be the cause of IPF. There is also a familial form of the disease, known as familial idiopathic pulmonary fibrosis. Additional research is being done to determine whether there is a genetic tendency to develop the disease, as well as to determine other causes of IPF.

Patients with IPF suffer similar symptoms to those with pulmonary fibrosis when their lungs lose the ability to transfer oxygen into the bloodstream. The symptoms include shortness of breath, particularly during or after physical activity; spasmodic, dry cough; gradual, unintended weight loss; fatigue and weakness; chest discomfort; clubbing, or enlargement of the ends of the fingers (or sometimes the toes) due to a buildup of tissue. These symptoms can greatly reduce IPF patients' quality of life. Pulmonary rehabilitation, and oxygen therapy can reduce the lifestyle-altering effects of IPF, but do not provide a cure.

Other mammalian fibrotic diseases that are amenable to treatment according to the invention include kidney disease, polycystic kidney disease, renal fibrotic disease, glomerular nephritis, liver cirrhosis, nephritis associated with systemic lupus, peritoneal fibrosis, liver fibrosis, polycystic ovarian syndrome, myocardial fibrosis, Grave's opthalmopathy, glaucoma, scarring, skin lesions, diabetic retinopathy, scleroderma, and Alzheimer's disease.

In order to develop a treatment for fibrotic disease, it is important to focus on the common pathway to the ultimate pathology that is shared by the disease states, regardless of cause or of tissue in which it is manifested. β-catenin plays a role in the development of fibrosis, and compounds that modulate this pathway are useful for treating fibrosis.

Wnt signaling plays an essential role in both the development and maintenance of multiple organ systems including the brain, intestines, skin and lung. A number of Wnt genes including Wnt2, Wnt5a, Wnt7b, Wnt11 and Wnt13 are expressed both in the developing and adult lung (Morrisey E. 2003, Am. J. Pathology, 162, 1393-7). In both epithelial (type 2 pneumocytes) and mesenchymal (myofibroblasts) cells, accumulation of nuclear β-catenin, a hallmark of activated Wnt signaling has been observed (Chilosi et al 2003, Am J. Pathology 162, 1495-1502). Importantly, increased proliferation of type 2 cells in IPF has been observed (Kawanami O et al. Lab Invest 1982, 46, 39-53 and Kasper M et al. Histol. Histopathol 1996, 11, 463-83). Furthermore, activation of Wnt signaling in the adjacent mesenchyme may further prevent the proper differentiation of the alveolar epithelium.

The well established bleomycin induced model of pulmonary fibrosis in transgenic Bat-Gal mice was used herein to demonstrate that aberrant activation of Wnt signaling in the lungs is induced after insult. Furthermore, utilizing a specific inhibitor of Wnt/β-catenin/CBP driven transcription (ICG-001, 5 mg/Kg/day s.c.) Wnt/β-catenin was inhibited by >95% as judged by β-galactosidase activity. ICG-001 is among the structures described in detail below.

The Wnt/β-catenin pathway initiates a signaling cascade critical in normal development of many organ systems including the lung (Morrisey E 2003 μm J Pathology, 162, 1393-7). The hallmark of this pathway is that it activates the transcriptional role of the multifunctional protein β-catenin. Canonical Wnt signaling inactivates GSK-3β, preventing β-catenin phosphorylation. This leads to accumulation of β-catenin in the cytoplasm and subsequent translocation to the nucleus (Behrens J, 2000, Ann. NY Acad. Sci. 910, 21-33.). A key step in the activation of target genes is the formation of a complex between β-catenin and members of the T-cell factor (TCF)/lymphoid enhancer factor (LEF-1) family of transcription factors. To generate a transcriptionally active complex, β-catenin recruits the transcriptional coactivators, Creb-Binding Protein (CBP) or its closely related homolog, p300 as well as other components of the basal transcription machinery.

Previously, aberrant Wnt/β-catenin signaling has been demonstrated in lung samples from patients with idiopathic pulmonary fibrosis (IPF) (Chilosi M. et al 2003 μm. J. Pathol. 162, 1495-1502) with increased nuclear β-catenin immunoreactivity and increased expression of two TCF/β-catenin regulated genes i.e. cyclin D1 and matrilysin (MMP7). An important role for increased MMP7 activity in pulmonary fibrotic disease is expected as MMP7 (−/−) mice are protected from bleomycin-induced pulmonary fibrosis (Zuo F et al PNAS 99, 6292, 2002).

ICG-001, a small molecule (FW 548) that selectively inhibits TCF/β-catenin transcription in a CBP-dependent fashion, was recently identified (Emami et al. Proc. Natl. Acad. Sci. USA 2004, 101, 12682-7 and McMillan and Kahn Drug Discovery Today 2005, 10, 1467-74). ICG-001 selectively blocks the β-catenin/CBP interaction without interfering with the highly homologous β-catenin/p300 interaction. Using a well established murine model of pulmonary fibrosis in transgenic Bat-Gal mice, we now demonstrate that ICG-001 (5 mg/Kg/day) blocks >95% of bleomycin-induced TCF/β-catenin transcription. Furthermore, ICG-001 at this dose not only halts but reverses disease progression, as judged by reduced mortality, histopathology and endogenous gene expression. Given the fact that currently no effective treatments for pulmonary fibrotic disease exist, inhibition of Wnt/β-catenin/CBP dependent transcription according to the invention appears to offer a novel therapeutic approach and provides industrial applicability.

Canonical Wnt signaling has been shown to promote self-renewal in a variety of tissue stem cells, including neuronal stem cells and hematopoeitic stem cells. However, activation of the canonical Wnt pathway can promote or inhibit differentiation depending on the experimental circumstances.

The present invention therefore is directed to conformationally constrained compounds which mimic the secondary structure of α-helix regions of biological peptide and proteins (also referred to herein as "α-helix mimetics" and chemical libraries relating thereto. Such compounds find use in treating fibrosis, including pulmonary fibrosis.

The α-helix mimetic structures of the present invention are useful as bioactive agents, including (but not limited to) use as diagnostic, prophylactic and/or therapeutic agents. The α-helix mimetic structure libraries of this invention are useful in the identification of such bioactive agents. In the practice of the present invention, the libraries may contain from tens to hundreds to thousands (or greater) of individual α-helix structures (also referred to herein as "members").

In one aspect of the present invention, a α-helix mimetic structure is disclosed having the following formula (I):

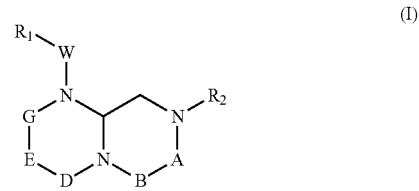

wherein A is —(C═O)—(CHR$_3$)—, B is —N—R$_4$—, D is —(CHR$_5$)— or —(C═O)—, E is —(ZR$_6$)— or —(C═O)—,
G is —(XR$_7$)$_n$—, —(CHR$_7$)—(NR$_8$)—, —(C═O)—(XR$_9$)—, or —(C═O)—, W is —Y(C═O)—, —(C═O)NH—, —(SO$_2$)— or nothing, Y is oxygen or sulfur, X and Z is independently nitrogen or CH, n=0 or 1; and R$_1$, R$_2$, R$_3$, R$_4$, R$_5$, R$_6$, R$_7$, R$_8$ and R$_9$, are the same or different and independently selected from an amino acid side chain moiety or derivative thereof, the remainder of the molecule, a linker and a solid support, and stereoisomers thereof.

More specifically, R$_1$, R$_2$, R$_3$, R$_4$, R$_5$, R$_6$, R$_7$, R$_8$ and R$_9$, are independently selected from the group consisting of aminoC$_{2-5}$alkyl, guanidineC$_{2-5}$alkyl, C$_{1-4}$alkylguanidinoC$_{2-5}$alkyl, diC$_{1-4}$alkylguanidino-C$_{2-5}$alkyl, amidinoC$_{2-5}$alkyl, C$_{1-4}$alkylamidino C$_{2-5}$alkyl, diC$_{1-4}$alkylamidinoC$_{2-5}$alkyl, C$_{1-3}$alkoxy, Phenyl, substituted phenyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), benzyl, substituted benzyl (where the substituents on the benzyl are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-3}$alkyl, nitro, carboxy, cyano, sulfuryl or hydroxyl), naphthyl, substituted naphthyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), bisphenyl methyl, substituted bis-phenyl methyl (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyridyl, substituted pyridyl, (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyridyl$C_{1-4}$alkyl, substituted pyridyl-$C_{1-4}$alkyl (where the pyridine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyrimidyl$C_{1-4}$alkyl, substituted pyrimidyl$C_{1-4}$alkyl (where the pyrimidine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), triazin-2-yl-$C_{1-4}$alkyl, substituted triazin-2-yl-$C_{1-4}$alkyl (where the triazine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), imidazolinylCalkyl, N-amidinopiperazinyl-N—$C_{0-4}$alkyl, hydroxy$C_{2-5}$alkyl, $C_{1-5}$alkylamino$C_{2-5}$alkyl, hydroxy$C_{2-5}$alkyl, $C_{1-5}$alkylamino$C_{2-5}$alkyl, $C_{1-5}$dialkylamino$C_{2-5}$alkyl, N-amidinopiperidinyl$C_{1-4}$alkyl and 4-aminocyclohexyl$C_{0-2}$alkyl.

In one embodiment, $R_1$, $R_2$, $R_6$ of E, and $R_7$, $R_8$ and $R_9$ of G are the same or different and represent the remainder of the compound, and $R_3$ or A, $R_4$ of B or $R_5$ of D is selected from an amino acid side chain moiety or derivative thereof. As used herein, the term "remainder of the compound" means any moiety, agent, compound, support, molecule, linker, amino acid, peptide or protein covalently attached to the α-helix mimetic structure at $R_1$, $R_2$, $R_5$, $R_6$, $R_7$, $R_8$ and/or $R_9$ positions. This term also includes amino acid side chain moieties and derivatives thereof.

As used herein, the term "amino acid side chain moiety" represents any amino acid side chain moiety present in naturally occurring proteins including (but not limited to) the naturally occurring amino acid side chain moieties identified in Table 1. Other naturally occurring amino acid side chain moieties of this invention include (but are not limited to) the side chain moieties of 3,5-dibromotyrosine, 3,5-diiodotyrosine, hydroxylysine, γ-carboxyglutamate, phosphotyrosine and phosphoserine. In addition, glycosylated amino acid side chains may also be used in the practice of this invention, including (but not limited to) glycosylated threonine, serine and asparagine.

TABLE 1

| Amino Acid Side Chain Moieties | |
| --- | --- |
| Amino Acid Side Chain Moiety | Amino Acid |
| —H | Glycine |
| —$CH_3$ | Alanine |

TABLE 1-continued

| Amino Acid Side Chain Moieties | |
| --- | --- |
| Amino Acid Side Chain Moiety | Amino Acid |
| —$CH(CH_3)_2$ | Valine |
| —$CH_2CH(CH_3)_2$ | Leucine |
| —$CH(CH_3)CH_2CH_3$ | Isoleucine |
| —$(CH_2)_4NH_3^+$ | Lysine |
| —$(CH_2)_3NHC(NH_2)NH_2^+$ | Arginine |
|  | Histidine |
| —$CH_2COO^-$ | Aspartic acid |
| —$CH_2CH_2COO^-$ | Glutamic acid |
| —$CH_2CONH_2$ | Asparagine |
| —$CH_2CH_2CONH_2$ | Glutamine |
|  | Phenylalanine |
|  | Tyrosine |
|  | Tryptophan |
| —$CH_2SH$ | Cysteine |
| —$CH_2CH_2SCH_3$ | Methionine |
| —$CH_2OH$ | Serine |
| —$CH(OH)CH_3$ | Threonine |
|  | Proline |
|  | Hydroxyproline |

In addition to naturally occurring amino acid side chain moieties, the amino acid side chain moieties of the present invention also include various derivatives thereof. As used herein, a "derivative" of an amino acid side chain moiety includes modifications and/or variations to naturally occurring amino acid side chain moieties. For example, the amino acid side chain moieties of alanine, valine, leucine, isoleucine and pheylalanine may generally be classified as lower chain alkyl, aryl, or arylalkyl moieties. Derivatives of amino acid side chain moieties include other straight chain or branched, cyclic or noncyclic, substitutes or unsubstituted, saturated or unsaturated lower chain alkyl, aryl or arylalkyl moieties.

As used herein, "lower chain alkyl moieties" contain from 1-12 carbon atoms, "lower chain aryl moieties" contain from 6-12 carbon atoms and "lower chain aralkyl moieties" contain from 7-12 carbon atoms. Thus, in one embodiment, the amino acid side chain derivative is selected from a $C_{1-12}$ alkyl, a $C_{6-12}$ aryl and a $C_{7-12}$ arylalkyl, and in a more preferred embodiment, from a $C_{1-7}$ alkyl, a $C_{6-10}$ aryl and a $C_{7-11}$ arylalkyl.

Amino side chain derivatives of this invention further include substituted derivatives of lower chain alkyl, aryl, and arylalkyl moieties, wherein the substituents is selected from (but are not limited to) one or more of the following chemical moieties: —OH, —OR, —COOH, —COOR, —CONH$_2$, —NH$_2$, —NHR, —NRR, —SH, —SR, —SO$_2$R, —SO$_2$H, —SOR and halogen (including F, Cl, Br and I), wherein each occurrence of R is independently selected from straight chain or branched, cyclic or noncyclic, substituted or unsubstituted, saturated or unsaturated lower chain alkyl, aryl, and aralkyl moieties. Moreover, cyclic lower chain alkyl, aryl and arylalkyl moieties of this invention include naphthalene, as well as heterocyclic compounds such as thiophene, pyrrole, furan, imidazole, oxazole, thiazole, pyrazole, 3-pyrroline, pyrrolidine, pyridine, pyrimidine, purine, quinoline, isoquinoline and carbazole. Amino acid side chain derivatives further include heteroalkyl derivatives of the alkyl portion of the lower chain alkyl and aralkyl moieties, including (but not limited to) alkyl and aralkyl phosphonates and silanes.

Representative $R_1$, $R_2$, $R_5$, $R_6$, $R_7$, $R_8$ and $R_9$ moieties specifically include (but are not limited to) —OH, —OR, —COR, —COOR, —CONH$_2$, —CONR, —CONRR, —NH$_2$, —NHR, —NRR, —SO$_2$R and —COSR, wherein each occurrence of R is as defined above.

In a further embodiment, and in addition to being an amino acid side chain moiety or derivative thereof (or the remainder of the compound in the case of $R_1$, $R_2$, $R_5$, $R_6$, $R_7$, $R_8$ and $R_9$), $R_1$, $R_2$, $R_5$, $R_6$, $R_7$, $R_8$ or $R_9$ may be a linker facilitating the linkage of the compound to another moiety or compound. For example, the compounds of this invention may be linked to one or more known compounds, such as biotin, for use in diagnostic or screening assay. Furthermore, $R_1$, $R_2$, $R_5$, $R_6$, $R_7$, $R_8$ or $R_9$ may be a linker joining the compound to a solid support (such as a support used in solid phase peptide synthesis) or alternatively, may be the support itself. In this embodiment, linkage to another moiety or compound, or to a solid support, is preferable at the $R_1$, $R_2$, $R_7$ or $R_8$ position, and more preferably at the $R_1$ or $R_2$ position.

In the embodiment wherein A is $-(C=O)-CHR_3-$, B is $-N-R_4$, D is $-(C=O)-$, E is $-(ZR_6)-$, G is $-(C=O)-(XR_9)-$, the α-helix mimetic compounds of this invention have the following general formula (III):

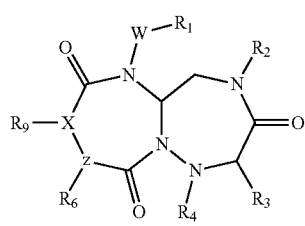

(III)

wherein $R_1$, $R_2$, $R_4$, $R_6$, $R_9$, W and X are as defined above, Z is nitrogen or CH (when Z is CH, then X is nitrogen). In a preferred embodiment, $R_1$, $R_2$, $R_6$, and $R_9$ represent the remainder of the compound, and $R_4$ is selected from an amino acid side chain moiety. In a more specific embodiment wherein A is $-O-CHR_3-$, B is $-NR_4-$, D is $-(C=O)-$, E is $-(ZR_6)-$, Gi is $(XR_7)_n-$, the α-helix mimetic compounds of this invention have the following formula (IV):

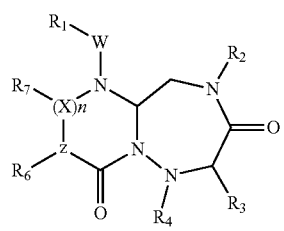

(IV)

wherein $R_1$, $R_2$, $R_4$, $R_6$, $R_7$, W, X and n are as defined above, and Z is nitrogen or CH (when Z is nitrogen, then n is zero, and when Z is CH, then X is nitrogen and n is not zero). In a preferred embodiment, $R_1$, $R_2$, $R_6$, and $R_7$ represent the remainder of the compound, and $R_4$ is selected from an amino acid side chain moiety. In this case, $R_6$ or $R_7$ may be selected from an amino acid side chain moiety when Z and X are CH, respectively.

The α-helix mimetic structures of the present invention may be prepared by utilizing appropriate starting component molecules (hereinafter referred to as "component pieces"). Briefly, in the synthesis of α-helix mimetic structures having formula (II), first and second component pieces are coupled to form a combined first-second intermediate, if necessary, third and/or fourth component pieces are coupled to form a combined third-fourth intermediate (or, if commercially available, a single third intermediate may be used), the combined first-second intermediate and third-fourth intermediate (or third intermediate) are then coupled to provide a first-second-third-fourth intermediate (or first-second-third intermediate) which is cyclized to yield the α-helix mimetic structures of this invention. Alternatively, the α-helix mimetic structures of formula (II) may be prepared by sequential coupling of the individual component pieces either stepwise in solution or by solid phase synthesis as commonly practiced in solid phase peptide synthesis.

Within the context of the present invention, a "first component piece" has the following formula S1

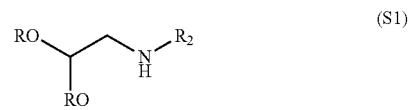

(S1)

Wherein $R_2$ as defined above, and R is a protective group suitable for use in peptide synthesis. Suitable R groups include alkyl groups and, in a preferred embodiment, R is a methyl group. Such first component pieces may be readily synthesized by reductive amination or substitution reaction by displacement of $H_2N-R_2$ from $CH(OR)_2-CHO$ or $CH(OR)_2-CH_2$-Hal (wherein Hal means a halogen atom).

A "second component piece" of this invention has the following formula S2:

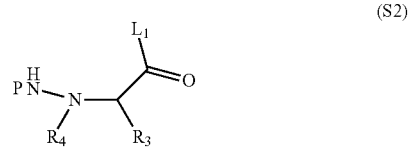

(S2)

Where $L_1$ is carboxyl-activation group such as halogen atom, $R_3$, $R_4$ is as defined above, and P is an amino protective group suitable for use in peptide synthesis. Preferred protective groups include t-butyl dimethylsilyl (TBDMS), t-Butyloxycarbonyl (BOC), Methylosycarbonyl (MOC), 9H-Fluorenylmethyloxycarbonyl (FMOC), and allyloxycarbonyl (Alloc). When L is $-C(O)NHR$, $-NHR$ may be a carboxyl protective group. N-hydrazino amino acids can be readily prepared according to the procedures of Vidal et al. (Tetrahedron Letters 39:8845-8848, 1998). The conversion of these compounds to the second component pieces of this invention may be readily achieved by activation of the carboxylic acid group of the N-protected hydrazine-amino acid. Suitable activated carboxylic acid groups include acid halides where X is a halide such as chloride or bromide, acid anhydrides where X is an acyl group such as acetyl, reactive esters such as an N-hydroxysuccinimide esters and pentafluorophenyl esters, and other activated intermediates such as the active intermediate formed in a coupling reaction using a carbodiimide such as dicyclohexylcarbodiimide (DCC).

A "third component piece" of this invention has the following formula S3:

(S3)

where G, E, and $L_1$ are as defined above. Suitable third component pieces are commercially available from a variety of sources or can be prepared by known methods in organic chemistry.

More specifically, the α-helix mimetic structures of this invention of formula (II) are synthesized by reacting a first component piece with a second component piece to yield a combined first-second intermediate, followed by either reacting the combined first-second intermediate with third component pieces sequentially to provide a combined first-second-third-fourth intermediate, and the cyclizing this intermediate to yield the α-helix mimetic structure.

The general synthesis of a α-helix having structure I' may be synthesized by the following technique. A first component piece 1 is coupled with a second component piece 2 by using coupling reagent such as phosgene to yield, after N-deprotection, a combined first-second intermediate 1-2 as illustrated below:

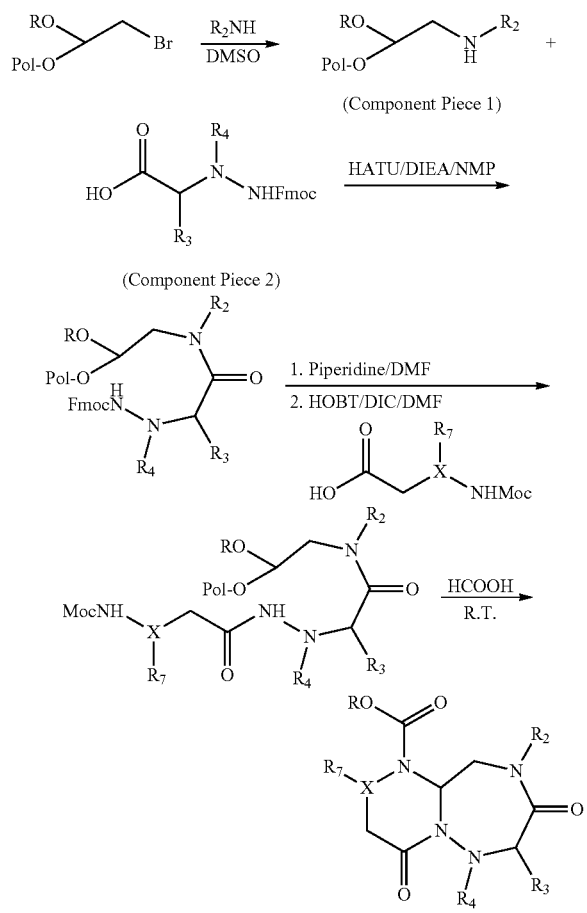

wherein $R_1$, $R_2$, $R_4$, $R_7$. Fmoc, Moc and X are as defined above, and Pol represents a polymeric support.

The synthesis of representative component pieces of this invention are described in Preparation Examples and Working Examples.

The α-helix mimetic structures of formula (III) and (IV) may be made by techniques analogous to the modular component synthesis disclosed above, but with appropriate modifications to the component pieces.

As mentioned above, the reverse-turn mimetics of U.S. Pat. No. 6,013,458 to Kahn, et al. are useful as bioactive agents, such as diagnostic, prophylactic, and therapeutic agents. The opiate receptor binding activity of representative reverse-turn mimetics is presented in Example 9 of said U.S. Pat. No. 6,013,458, wherein the reverse-turn mimetics of this invention were found to effectively inhibit the binding of a radio-labeled enkephalin derivative to the δ and μ opiate receptors, of which data demonstrates the utility of these reverse-turn mimetics as receptor agonists and as potential analgesic agents.

The α-helix mimetic structures of the present invention will be useful as bioactive agents, such as diagnostic, prophylactic, and therapeutic agents.

Therefore, since the compounds according to the present invention are of α-helix mimetic structures, it may be useful for modulating a cell signaling transcription factor related peptides in a warm-blooded animal, comprising administering to the animal an effective amount of the compound of formula (I).

A particular compound, referred to as ICG-001, is shown below as compound V:

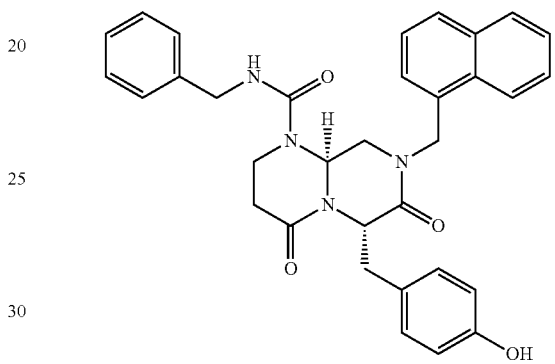

Further, the α-helix mimetic structures of the present invention may also be effective for inhibiting transcription factor/coactivator and transcription factor corepressor interactions.

Therefore, it is an object of the present invention to provide a pharmaceutical composition comprising a safe and effective amount of the compound having general formula (VI) and pharmaceutically acceptable carrier, which can be used for treatment of fibrotic disorders modulated by TGF-β signaling pathway.

In another aspect of this invention, libraries containing α-helix mimetic structures of the present invention are disclosed. Once assembled, the libraries of the present invention may be screened to identify individual members having bioactivity. Such screening of the libraries for bioactive members may involve; for example, evaluating the binding activity of the members of the library or evaluating the effect the library members have on a functional assay. Screening is normally accomplished by contacting the library members (or a subset of library members) with a target of interest, such as, for example, an antibody, enzyme, receptor or cell line. Library members, which are capable of interacting with the target of interest, are referred to herein as "bioactive library members" or "bioactive mimetics". For example, a bioactive mimetic may be a library member which is capable of binding to an antibody or receptor, which is capable of inhibiting an enzyme, or which is capable of eliciting or antagonizing a functional response associated, for example, with a cell line. In other words, the screening of the libraries of the present invention determines which library members are capable of interacting with one or more biological targets of interest. Furthermore, when interaction does occur, the bioactive mimetic (or mimetics) may then be identified from the library members. The identification of a single (or limited number) of bioactive mimetic(s) from the library yields α-helix mimetic structures which are themselves biologically active, and thus useful as diagnostic, prophylactic or therapeutic agents, and may further be used to significantly advance identification of lead compounds in these fields.

In another aspect of this invention, methods for constructing the libraries are disclosed. Traditional combinatorial chemistry techniques (see, e.g., Gallop et al., *J. Med. Chem.* 37:1233-1251, 1994) permit a vast number of compounds to be rapidly prepared by the sequential combination of reagents to a basic molecular scaffold. Combinatorial techniques have been used to construct peptide libraries derived from the naturally occurring amino acids. For example, by taking 20 mixtures of 20 suitably protected and different amino acids and coupling each with one of the 20 amino acids, a library of 400 (i.e., $20^2$) dipeptides is created. Repeating the procedure seven times results in the preparation of a peptide library comprised of about 26 billion (i.e., $20^8$) octapeptides.

Specifically, synthesis of the peptide mimetics of the library of the present invention may be accomplished using known peptide synthesis techniques, for example, the General Scheme of [4,4,0] α-helix Mimetic Library as follows:

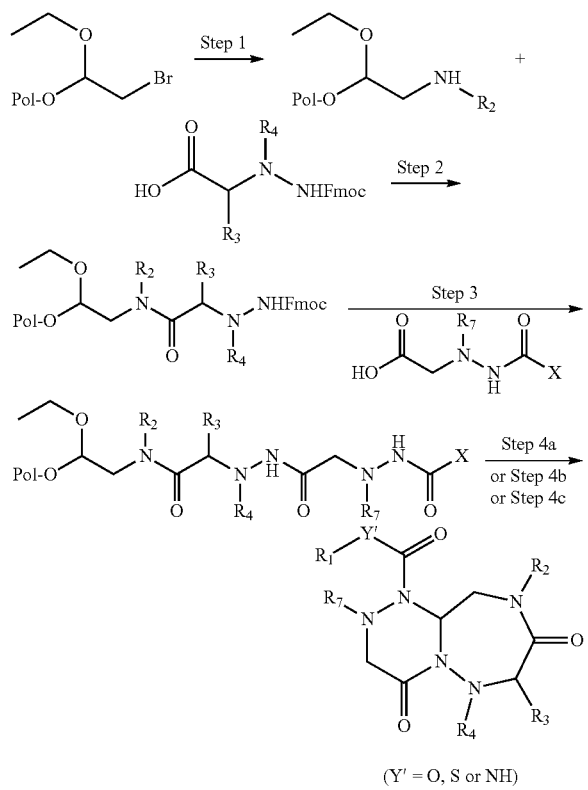

(Y' = O, S or NH)

Synthesis of the peptide mimetics of the libraries of the present invention was accomplished using a FlexChem Reactor Block which has 96 well plates by known techniques. In the above scheme Pa represents a bromoacetal resin (Advanced ChemTech) and detailed procedure is illustrated below.

Step 1

A bromoacetal resin (37 mg, 0.98 mmol/g) and a solution of $R_2$-amine in DMSO (1.4 mL) were placed in a Robbins block (FlexChem) having 96 well plates. The reaction mixture was shaken at 60° C. using a rotating oven [Robbins Scientific] for 12 hours. The resin was washed with DMF, MeOH, and then DCM Step 2

A solution of available Fmoc hydrazine Amino Acids (4 equiv.), PyBop (4 equiv.), HOAt (4 equiv.), and DIEA (12 equiv.) in DMF was added to the resin. After the reaction mixture was shaken for 12 hours at room temperature, the resin was washed with DMF, MeOH, and them DCM.

Step 3

To the resin swollen by DMF before reaction was added 25% piperidine in DMF and the reaction mixture was shaken for 30 min at room temperature. This deprotection step was repeated again and the resin was washed with DMF, Methanol, and then DCM. A solution of hydrazine acid (4 equiv.), HOBt (4 equiv.), and DIC (4 equiv.) in DMF was added to the resin and the reaction mixture was shaken for 12 hours at room temperature. The resin was washed with DMF, MeOH, and then DCM.

Step 4a (where Hydrazine Acid is MOC Carbamate)

The resin obtained in Step 3 was treated with formic acid (1.2 mL each well) for 18 hours at room temperature. After the resin was removed by filtration, the filtrate was condensed under a reduced pressure using SpeedVac [SAVANT] to give the product as oil. The product was diluted with 50% water/acetonitrile and then lyophilized after freezing.

Step 4b (where Fmoc Hydrazine Acid is Used to Make Urea Through Isocynate)

To the resin swollen by DMF before reaction was added 25% piperidine in DMF and the reaction mixture was shaken for 30 min at room temperature. This deprotection step was repeated again and the resin was washed with DMF, Methanol, then DCM. To the resin swollen by DCM before reaction was added isocynate (5 equiv.) in DCM. After the reaction mixture was shaken for 12 hours at room temperature the resin was washed with DMF, MeOH, then DCM. The resin was treated with formic acid (1.2 mL each well) for 18 hours at room temperature. After the resin was removed by filtration, the filtrate was condensed under a reduced pressure using SpeedVac [SAVANT] to give the product as oil. The product was diluted with 50% water/acetonitrile and then lyophilized after freezing.

Step 4c (where Fmoc-Hydrazine Acid is Used to Make Urea Through Active Carbamate)

To the resin swollen by DMF before reaction was added 25% piperidine in DMF and the reaction mixture was shaken for 30 min at room temperature. This deprotection step was repeated again and the resin was washed with DMF, MeOH, and then DCM. To the resin swollen by DCM before reaction was added p-nitrophenyl chloroformate (5 equiv.) and diisopropyl ethylamine (5 equiv.) in DCM. After the reaction mixture was shaken for 12 hours at room temperature, the resin was washed with DMF, MeOH, and then DCM. To the resin was added primary amines in DCM for 12 hours at room temperature and the resin was washed with DMF, MeOH, and then DCM. After reaction the resin was treated with formic acid (1.2 mL each well) for 18 hours at room temperature. After the resin was removed by filtration, the filtrate was condensed under a reduced pressure using SpeedVac [SAVANT] to give the product as oil. The product was diluted with 50% water/acetonitrile and then lyophilized after freezing.

It should be understood that the examples and embodiments described herein are for illustrative purposes only and that various modifications or changes in light thereof will be suggested to persons skilled in the art and are to be included within the spirit and purview of this application.

Example 1

Effect of ICG-001 on Pulmonary Fibrosis

Murine models of bleomycin induced fibrosis have been developed in order to study fibrotic disease progression. Bleomycin induced murine fibrosis has been shown to lead to aberrant alveolar epithelial repair, with increased metaplastic alveolar cells that apparently do not properly differentiate to a type I phenotype (Adamson and Bowden 1979 Am J Pathol. 1979 August; 96(2):531-44.). Utilizing this model, it is demonstrated in this Example that the Wnt/β-catenin pathway plays a critical role in the development of pulmonary fibrosis and validates that the inhibition of this pathway with ICG-001 represents a therapy for the treatment of pulmonary fibrotic disease.

Using this murine model of pulmonary fibrosis in transgenic Bat-Gal mice, ICG-001 (5 mg/Kg/day) blocked >95% of bleomycin-induced TCF/β-catenin transcription. Furthermore, ICG-001 at this dose not only halted but reversed disease progression, as judged by reduced mortality, histopathology and endogenous gene expression.

FIG. 1 shows lung sections taken from Bat-Gal transgenic mice. These mice have a Beta-Galactosidase transgene driven by a TCF/Catenin driven promoter (i.e. a read out for activated Wnt/catenin signaling). The mice were given intratracheal saline or bleomycin and either treated with ICG-001 (5 mgs/Kg/day subcutaneously) or saline as vehicle control. The mice were sacrificed and the lungs sectioned and stained with X-Gal (blue color) A) intratracheal bleo+saline. B) intracheal bleo+ICG-001 C) saline+saline.

The dose was selected because ICG-001 reduces TCF/13-Catenin driven O-Galactosidase expression >95% at 5 mgs/Kg/day.

Figure 2:
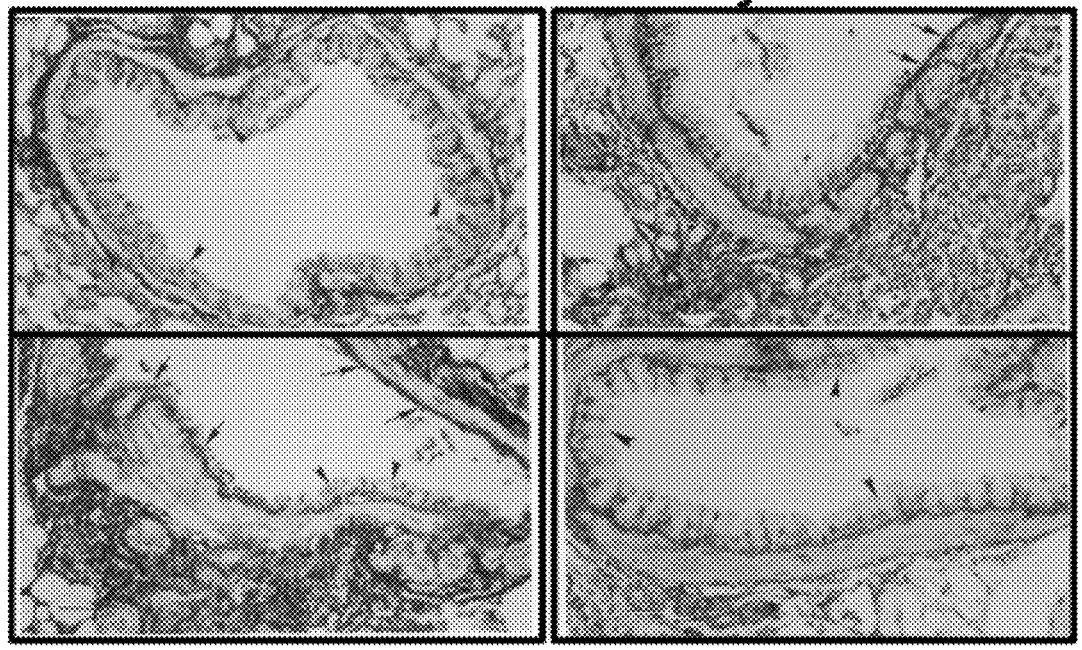
FIG. 2 depicts lung sections taken from C57/B16 mice treated with intratracheal bleomeycin (lower left) or saline (upper left) for 5 days and stained with trichrome (red color) to stain collagen.

FIG. 2 shows lung sections taken from C57/B16 mice treated with intratracheal bleomeycin (lower left) or saline (upper left) for 5 days and stained with trichrome (red color) to stain collagen. There is an absence of airway epithelium in lower left compared to upper left (see arrow heads) and extensive collagen deposition (lower left). On the sixth day, either saline (upper right) or ICG-001 (5 mgs/Kg/day) was administered for 10 days after which the mice were sacrificed and sectioned. Of interest is the upper right (saline treatment) showing lack of normal airway epithelialization, extensive collagen deposition and intra-airway hypercellularity (fibroblasts and inflammatory influx). After treatment with ICG-001, the airway looks essentially normal (compare to untreated (saline) control) (upper left), with normal collagen levels. The mice also regained normal body weight and survived (untreated controls did not).

Figure 3:
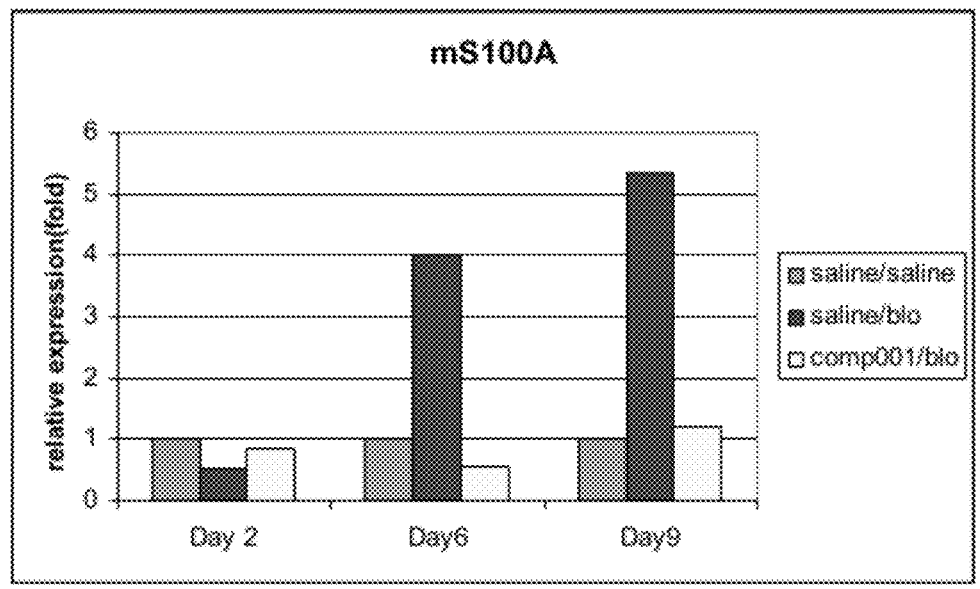
FIG. 3 shows RT-PCR data for S100A4 and collagen1A2, which are increased in the bleomycin treated mice (treated with saline control). Message is reduced essentially to negative control (i.e. saline/saline mice) levels by ICG-001 treatment (5 mgs/Kg/day s.c.)
Figure 3:
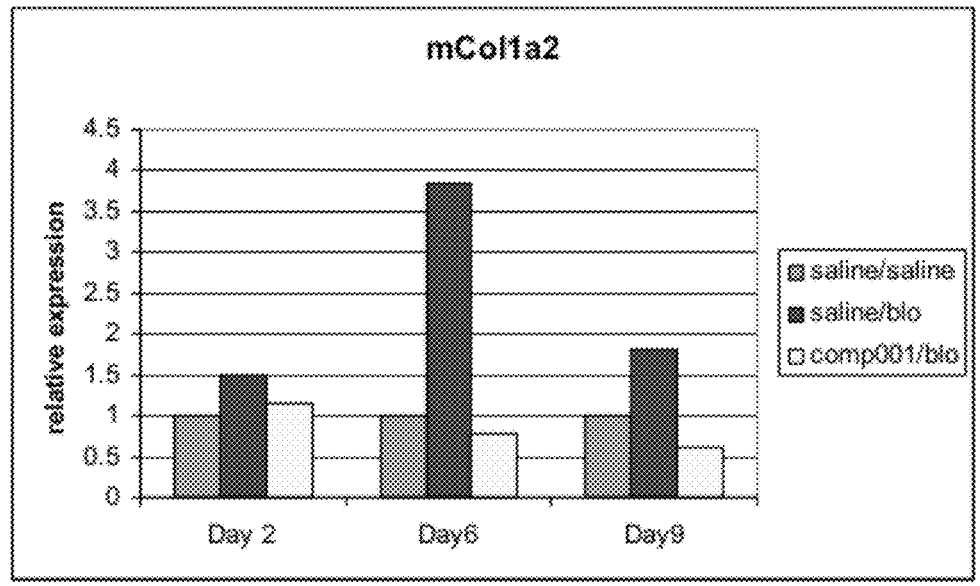

FIG. 3 shows RT-PCR data for S100A4 and collagen1A2, which are increased in the bleomycin treated mice (treated with saline control). Message is reduced essentially to negative control (i.e. saline/saline mice) levels by ICG-001 treatment (5 mgs/Kg/day s.c.)

Figure 4:
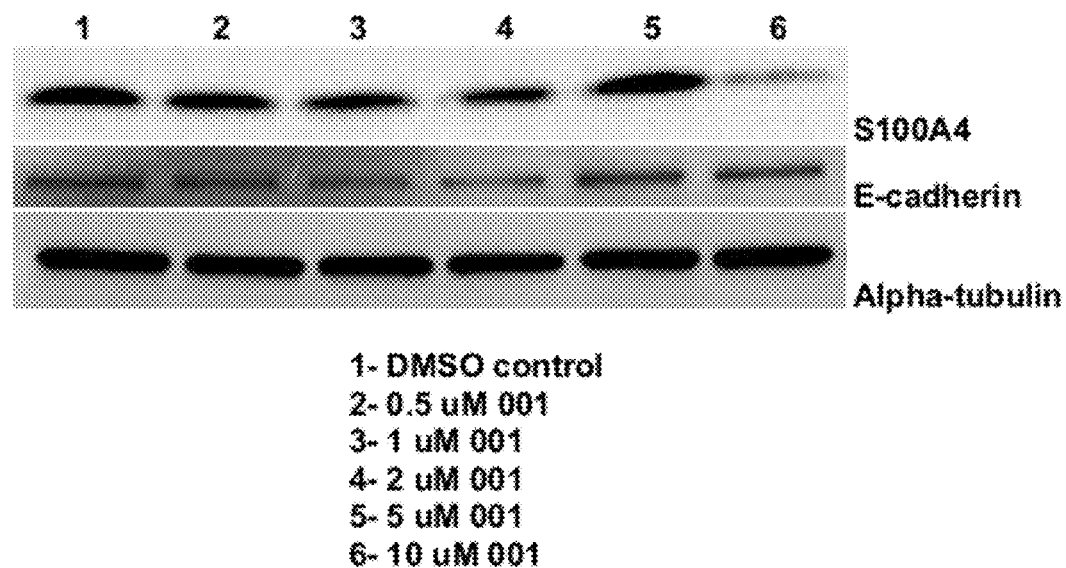
FIG. 4 shows the results of IPF patient fibroblasts after culture in RPMI1640+10% FBS for 2 days and treatment with ICG-001. Western blots for S100A4 (also known as FSP-1 or fibroblast specific protein-1) and E-Cadherin were performed on whole cell lysates. ICG-001 decreased S100A4 expression and increased E-cadherin expression.

As shown in FIG. 4, IPF patient fibroblasts were cultured in RPMI1640±10% FBS for 2 days and treated with ICG-001. Western blots for S100A4 (also know as FSP-1 or fibroblast specific protein-1) and E-Cadherin were performed on whole cell lysates. ICG-001 decreased S100A4 expression and increased E-cadherin expression (this is also true at the mRNA level). These data demonstrate that ICG-001 mediates a mesenchymal to epithelial transition that is essential for normal healing, re-epithelialization and ameliorization of fibrosis.

All patents, patent applications, provisional applications, and publications referred to or cited herein are incorporated by reference in their entirety, including all figures and tables, to the extent they are not inconsistent with the explicit teachings of this specification.

We claim:

1. A pharmaceutical composition, comprising a compound having the following general formula (I):

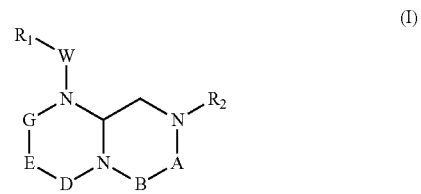

wherein A is —(CHR$_3$)—(C=O)—, B is —(NR$_4$)—, D is —(CHR$_5$)— or —(C=O)—, E is —(ZR$_6$)—, —(C=O)—, G is —(XR$_7$)$_n$—, —(CHR$_7$)—(NR$_8$)—, —(C=O)—(XR$_9$)—, or —(C=O)—, W is —Y(C=O)—, —(C=O)NH—, —(SO$_2$)— or nothing, Y is oxygen or sulfur, X and Z is independently nitrogen or CH, n=0 or 1;

and wherein R$_1$, R$_2$, R$_3$, R$_4$, R$_5$, R$_6$, R$_7$, R$_8$ and R$_9$ are the same or different and independently selected from the group consisting of aminoC2-5alkyl, guanidinoC2-5alkyl, C1-4-alkylguanidinoC2-5alkyl, diC1-4alkylguanidino-C2-5alkyl, amidinoC2-5alkyl, C1-4-alkylamidinoC2-5 alkyl, diC1-4alkylamidinoC2-5 alkyl, C1-3 alkoxy, Phenyl, substituted phenyl (where the substituents are independently selected from one or more of amino, amidino, guanidino, hydrazino, amidrazonyl, C1-4-alkylamino, C1-4-dialkylamino, halogen, perfluoro C1-4-alkyl, C1-4-alkyl, C1-3alkoxy, nitro, carboxy, cyano, sulfuryl or hydroxyl), benzyl, substituted benzyl (where the substituents on the benzyl are independently selected from one or more of amino, amidino, guanidino, hydrazino, amidrazonyl, C1-4-alkylamino, C1-4-dialkylamino, halogen, perfluoro C1-4-alkyl, C1-4alkyl, C1-3alkoxy, nitro, carboxy, cyano, sulfuryl or hydroxyl), naphthyl, substituted naphthyl (where the substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3 alkoxy, nitro, carboxy, cyano, sulfuryl or hydroxyl), bis-phenyl methyl, substituted bis-phenyl methyl (where the substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), pyridyl, substituted pyridyl, (where the substituents are independently selected from one or more of amino, amidino, guanidino, hydrazino, amidrazonyl, C1-4-alkylamino, C1-4-dialkylamino, halogen, perfluoro C1-4alkyl, C1-4alkyl, C1-3alkoxy, nitro, carboxy, cyano, sulfuryl or hydroxyl), pyridylC1-4alkyl, substituted pyridylC1-4alkyl (where the pyridine substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3 alkoxy, nitro, carboxy, cyano, sulfuryl or hydroxyl), pyrimidylC1-4alkyl, substituted pyrimidylC1-4alkyl (where the pyrimidine substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy or nitro, carboxy, cyano, sulfuryl or hydroxyl), triazin-2-yl-C1-4alkyl, substituted triazin-2-yl-C1-4alkyl (where the triazine substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3 alkoxy, nitro, carboxy, cyano, sulfuryl or hydroxyl), imidazoC1-4alkyl, substituted imidazol C1-4-alkyl (where the imidazole substituents are independently selected from one or more of amino, amidino, guanidino, hydrazino, amidrazonyl, C1-4-alkylamino, C1-4-dialkylamino, halogen, perfluoro C1-4-alkyl, C1-4-alkyl, C1-3alkoxy, nitro, carboxy, cyano, sulfuryl or hydroxyl), imidazolinylC1-4alkyl, N-amidinopiperazinyl-N—C0-4alkyl, hydroxyC2-5alkyl, C1-5 alkylaminoC2-5 alkyl, hydroxyC2-5 alkyl, C1-5 alkylaminoC2-5 alkyl, C1-5dialkylaminoC2-5alkyl, N-amidinopiperidinylC1-4alkyl and 4-aminocyclohexylC0-2alkyl, a naturally occurring amino acid side chain moiety or derivative thereof, and stereoisomers thereof.

2. The pharmaceutical composition of claim 1, wherein A is —(CHR3)-(C═O)—, B is —(NR4)-, D is (C═O)—, E is —(ZR6)-, G is —(C═O)—(XR9)-, and the compound has the following general formula (III):

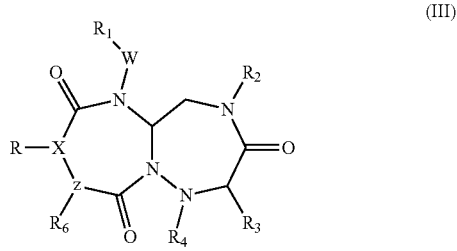

(III)

wherein $R_1$, $R_2$, $R_4$, $R_6$, $R_9$, W and X are as defined in claim 1, Z is nitrogen or CH (when Z is CH, the X is nitrogen).

3. The pharmaceutical composition of claim 1, wherein when A is —O—CHR3-, B is —NR4-, D is —(C═O)—, E is —(ZR6)-, G is (XR7)n-, the α-helix mimetic compound has the formula (IV):

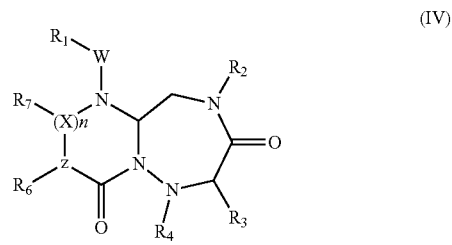

(IV)

wherein Z is nitrogen or CH, and when Z is nitrogen, then n is zero; when Z is CH, then X is nitrogen and n is not zero or $X_{(n)}$ is zero.

4. The pharmaceutical composition of claim 3, wherein R4 is selected from an amino acid side chain moiety and R6 or R7 may be selected from an amino acid side chain moiety when Z and X are CH, respectively.

5. The pharmaceutical composition according to claim 1 in which the composition comprises a safe and effective amount of the compound, and a pharmaceutically acceptable carrier.

6. The pharmaceutical composition of claim 1 wherein said compound inhibits Wnt/catenin signaling in fibrotic disease.

7. The pharmaceutical composition of claim 1, wherein said compound is an antifibrotic and/or an anti-proliferative agent.

8. The pharmaceutical composition of claim 7, wherein said antifibrotic agent has at least one activity selected from the group consisting of reparation or prevention of pathological polymerization of collagen in lung fibrosis.

9. The pharmaceutical composition of claim 7, wherein said antifibrotic agent has at least one activity selected from the group consisting of reparation and normalization of existing pathological fibrotic tissues.

* * * * *